United States Patent
Smith et al.

(10) Patent No.: US 6,244,712 B1
(45) Date of Patent: Jun. 12, 2001

(54) OPTICAL SCANNING SPECTROSCOPIC APPARATUS AND ASSOCIATED METHOD

(75) Inventors: Matthew H. Smith, Madison; Lloyd W. Hillman, Huntsville; Kurt R. Denninghoff, Birmingham, all of AL (US); Russell A. Chipman, San Jose, CA (US)

(73) Assignee: University of Alabama in Huntsville, Huntsville, AL (US)

( * ) Notice: Subject to any disclaimer, the term of this patent is extended or adjusted under 35 U.S.C. 154(b) by 0 days.

(21) Appl. No.: 09/405,771

(22) Filed: Sep. 27, 1999

(51) Int. Cl.[7] ....................................................... A61B 3/10
(52) U.S. Cl. ............................................................ 351/221
(58) Field of Search ...................................... 351/205, 206, 351/211, 212, 221; 359/350, 351, 352; 600/318, 310, 504, 558, 479; 606/4

(56) References Cited

U.S. PATENT DOCUMENTS

| | | |
|---|---|---|
| 5,119,814 | 6/1992 | Minnich . |
| 5,308,919 | 5/1994 | Minnich . |
| 5,776,060 | 7/1998 | Smith et al. . |
| 5,815,242 | 9/1998 | Anderson et al. . |
| 5,835,262 | * 11/1998 | Iketaki et al. ........................ 359/352 |
| 5,935,076 | 8/1999 | Smith et al. . |

* cited by examiner

Primary Examiner—George Manuel
(74) Attorney, Agent, or Firm—Alston & Bird LLP

(57) ABSTRACT

An improved optical scanning spectroscopic method and apparatus is provided that alternately scans the posterior portion of an eye with laser signals emitted by different ones of a plurality of lasers such that a data frame can be constructed that includes interlaced portions formed from signals returning from the posterior portion of the eye in response to illumination by laser signals emitted by different ones of the plurality of lasers. As such, the same data frame includes data attributable to the reflection of laser signals from each of the plurality of lasers even though the subject's eye is not subjected to simultaneous illumination by each of the lasers, thereby protecting the subject's eye. According to one further aspect of the invention, the optical scanning spectroscopic method and apparatus can illuminate the posterior portion of the subject's eye in response to a trigger at a predetermined point in the cardiac cycle of the subject such that the resulting data frame relates to at least a predetermined portion of the cardiac cycle of the subject, thereby permitting a detailed analysis of one or more phases of the cardiac cycle of the subject.

23 Claims, 5 Drawing Sheets

OPTICAL SCANNING SPECTROSCOPIC APPARATUS AND ASSOCIATED METHOD

GOVERNMENT RIGHTS

This invention was made with Government support under grant number DAMD17-98-1-8007 awarded by the U.S. Army Medical Research Acquisitions Activity. The Government may have certain rights in the invention.

FIELD OF THE INVENTION

The present invention relates generally to an optical imaging apparatus and associated methods and, more particularly, to an optical scanning spectroscopic apparatus and associated methods for generating images of the posterior portion of a subject's eye.

BACKGROUND OF THE INVENTION

By examining the posterior portions of a subject's eye, such as the retinal vessels and the choroidal vessels, a significant amount of data can be collected for various diagnostic and analytical applications. For example, the blood oxygen saturation or blood oxygen content of the blood in the retinal vessels is determinative of the arteriovenous oxygen difference as described by U.S. Pat. No. 5,308,919 to Thomas E. Minnich, U.S. Pat. No. 5,776,060 to Matthew H. Smith, et. al., and U.S. Pat. No. 5,935,076 to Matthew H. Smith, et. al. Based upon the arteriovenous oxygen difference, the cardiac output of the subject can be determined in order to assist in post-operative monitoring and the management of critically ill patients. By monitoring the blood oxygen saturation, the loss of blood can also be detected and the rate and quantity of blood loss over time can be estimated as described by U.S. Pat. No. 5,119,814 to Thomas E. Minnich.

In addition to blood oxygen saturation, retinal tissue perfusion can be monitored by observing the color of cytochromes, such as cytochrome oxidase a3, within the tissue cells. Further, by observing the magnitude of the choroidal reflectance pulsation across the cardiac cycle, such as with a pulse oximeter, the choroidal oxygenation can also be monitored. See J. P. de Kock, L. Tarrassenko, C. J. Glynn, A. R. Hill, "Reflectance Pulse Oximetry Measurements from the Retinal Fundus," IEEE Transactions on Biomedical Engineering, vol. 40, no. 8, 817–23 (1993). In addition to the foregoing examples, a number of other anatomic features and physiological parameters, such as the degree of melanin pigmentation of the fundus, can be determined by examining the posterior portion of a subject's eye, as described by F. C. Delori, K. P. Phlibsen, "Spectral reflectance of the human ocular fundus," Applied Optics, vol. 28, no. 6, 1061–77 (1989).

In order to examine the posterior portion of a subject's eye, several non-invasive techniques have been developed. In this regard, the traditional technique for examining the posterior portions of a subject's eye is fundus photography. Fundus photography illuminates a subject's eye with a flash of white light. Fundus photography then detects the light returning from the subject's eye, such as a result of the reflection of a portion of the light from the retinal and choroidal vessels, as well as the reflection and scattering of portions of the light from other features of the posterior portion of the subject's eye. Since the subject's eye is initially illuminated with white light, fundus photography typically spectrally separates the light that returns from the subject's eye in order to separately evaluate the signals that return from the subject's eye at different wavelengths of interest.

Because traditional fundus photography involves illuminating the subject's eye with a flash of white light, care must generally be taken to ensure that the subject's eye is not exposed to excessively high levels of light that could harm the subject's eye. In this regard, the Food and Drug Administration has defined maximum allowable amounts of light to which an eye can be exposed over a certain time period. As such, the intensity of the flash of white light must generally be maintained below some relatively low threshold, such as below about 100 mJ/cm$^2$ in order to protect the subject's eye. Since the flash of white light must generally be maintained below some threshold, the resulting signal to noise ratio of the signals returning from the posterior portion of the subject's eye is also relatively low in comparison to the higher signal to noise ratios that would be obtained if the flash of white light could have a greater intensity. As a result of the relatively low signal to noise ratio, at least some of the signals returning from the posterior portions of the subject's eye generally are lost in the noise, and the overall validity or credibility of the signals returning from the posterior portions of the subject's eye is subject to more questions.

Even though the flash of white light that illuminates a subject's eye in traditional fundus photography is somewhat limited in order to protect the subject's eye, the flash of white light is still generally sufficiently intense to prevent closely spaced, serial measurements from being obtained. In this regard, the flash of white light is still sufficiently intense to cause the pupil of the subject's eye to constrict and, in some instances, to cause the metabolism of the subject's eye to be altered. In order to monitor the posterior portions of the subject's eye under consistent conditions, traditional fundus photography must therefore wait until the subject's pupil is no longer constricted prior to collecting another image of the posterior portions of the subject's eye, thereby disadvantageously delaying the entire examination process.

More recently, scanning laser opthalmoscopes have addressed at least some of the shortcomings of traditional fundus photography. For a general description of scanning laser opthalmoscopes, see Noninvasive Diagnostic Techniques in Ophthalmology, Barry R. Masters, editor, Chapter 22, Scanning Laser Ophthalmoscope, by Robert H. Webb, Springer-Verlag, N.Y. (1990). Conventional scanning laser opthalmoscopes have a single laser source. The scanning laser opthalmoscope scans the laser signals emitted by the laser source in a predetermined pattern across posterior portions of a subject's eye to thereby define a frame having a number of scan lines. Since a single laser is employed, the resulting image will only provide information relating to the posterior portion of the eye at the one particular wavelength.

A more recent scanning laser opthalmoscope developed by OPTOS P.L.C. of Fife, United Kingdom apparently includes three laser sources, each of which emits light of a different wavelength. This scanning laser opthalmoscope is designed to simultaneously illuminate the subject's eye by scanning laser signals emitted by each of the three lasers across the posterior portion of the subject's eye.

This scanning laser opthalmoscope also typically includes dichroic beam splitters for separating the signals that return from the posterior portions of the subject's eye based upon the wavelength of the return signals. As such, the return signals attributable to the laser signals emitted by each of the laser sources are effectively separated and can therefore be individually analyzed.

Since this more recent scanning laser opthalmoscope simultaneously illuminates a subject's eye with the laser signals emitted by each of the laser sources, this scanning laser opthalmoscope may also have the potential to expose the subject's eye to excessive amounts of light. As such, the intensity of the laser signals emitted by each of the laser sources is generally maintained at a relatively low level, such as below about 10 uW such that the cumulative intensity of the laser signals remains safe for the subject's eye. As such, the signal-to-noise ratio of the signals returning from the posterior portions of the subject's eye is therefore correspondingly reduced relative to the signal-to-noise ratio of the return signals that would be possible if the intensity of the laser signals emitted by each of the laser sources were not reduced in order to protect the subject's eye. At least some of the signals returning from the posterior portion of the subject's eye will therefore be lost in the noise and the overall validity of the return signals will be somewhat more questionable due to the lower signal-to-noise ratio.

In addition, it has been proposed that a scanning laser opthalmoscope could sequentially scan the posterior portions of a subject's eye with the laser signals emitted by the plurality of laser sources. See U.S. Pat. No. 5,815,242 to Douglas C. Anderson, et al. and assigned to OPTOS P.L.C. that describes a scanning laser opthalmoscope having first, second and third laser sources. In operation, the scanning laser opthalmoscope initially scans the posterior portions of the eye with the laser signals emitted by the first laser so as to create a first data frame based upon the return signals. Thereafter, the scanning laser opthalmoscope scans the posterior portions of the eye with laser signals emitted by the second laser source in order to create a second data frame. Finally, the scanning laser opthalmoscope scans the posterior portions of the eye with the laser signals emitted by the third laser source in order to create a third data frame. While sequentially scanning the posterior portions of the eye with the laser signals emitted by the different laser sources permits the laser sources to emit laser signals having a greater intensity, the overall examination process takes longer since separate data frames must be constructed for the laser signals emitted by each of the laser sources. In addition, since the posterior portions of the eye are scanned with the laser signals emitted by each of the different laser sources at different intervals of time, the test conditions may change between the times at which the eye is exposed to laser signals from different ones of the laser sources. For example, the subject may move slightly, thereby altering the area of the peripheral portion of the eye that is illuminated and therefore examined. Alternatively, the subject's pupil may constrict as a result of the laser illumination. Since the test conditions can change between the time at which the laser signals emitted by one of the laser sources are scanned across the posterior portions of the eye and the time at which the laser signals emitted by another one of the laser sources are scanned across the posterior portions of the eye, the consistency and correlation between the data frames attributable to the laser signals emitted by each of the laser sources are limited.

Accordingly, while several techniques have been developed for examining the posterior portions of a subject's eye, each of these techniques is somewhat limited. As such, an improved method and apparatus for examining the posterior portion of an eye is therefore desired which does not expose a subject's eye to excessive illumination. In addition, it would be desirable to examine the posterior portions of a subject's eye during specific predetermined portions of the subject's cardiac cycle since a number of the features that are being examined are at least somewhat dependent upon the phase of the cardiac cycle. Traditional fundus photography and scanning laser opthalmoscopes have not generally considered the phase of the cardiac cycle of the subject, but have, instead, obtained images or other data related to the posterior portions of the subject's eye without regard to the phase of the cardiac cycle of the subject. As such, the variations in those features of the posterior portion of the subject's eye that are dependent upon the phase of the cardiac cycle of the subject have typically not been taken into account.

SUMMARY OF THE INVENTION

An improved optical scanning spectroscopic method and apparatus is therefore provided according to the present invention. The optical scanning spectroscopic method and apparatus of the present invention alternately scans the posterior portion of an eye with laser signals emitted by different ones of a plurality of lasers such that a data frame can be constructed that includes interlaced portions formed from signals returning from the posterior portion of the eye in response to illumination by laser signals emitted by different ones of the plurality of lasers. As such, the same data frame includes data attributable to the reflection of laser signals from each of the plurality of lasers even though the subject's eye is not subjected to simultaneous illumination by each of the lasers, thereby protecting the subject's eye. According to one further aspect of the present invention, the optical scanning spectroscopic method and apparatus can illuminate the posterior portion of the subject's eye in response to a trigger at a predetermined point in the cardiac cycle of the subject such that the resulting data frame relates to at least a predetermined portion of the cardiac cycle of the subject, thereby permitting a detailed analysis of one or more phases of the cardiac cycle of the subject.

The optical scanning spectroscopic apparatus includes a plurality of lasers for emitting laser signals having different respective wavelengths. For example, the optical scanning spectroscopic apparatus can include first, second, third and fourth lasers for emitting laser signals having first, second, third and fourth wavelengths, respectively. The optical scanning spectroscopic apparatus also includes a scanner for repeatedly scanning the laser signals emitted by the plurality of lasers across the posterior portion of a subject's eye. The optical scanning spectroscopic apparatus can also include a detector for detecting signals returning from the posterior portion of the eye in response to illumination by the laser signals. As such, a data frame having a number of interlaced portions can be formed from the returning signals. In this regard, the optical scanning spectroscopic apparatus also includes a controller for alternately activating different ones of the plurality of lasers while the scanner scans the laser signals across the posterior portion of the eye. As such, the adjacent interlaced portions of the resulting data frame are formed from signals returning from the posterior portion of the eye in response to illumination by laser signals emitted by different ones of the plurality of lasers.

For example, in the embodiment in which the optical scanning spectroscopic apparatus includes first, second, third and fourth lasers, the controller alternately activates the first, second, third and fourth lasers while the scanner scans the laser signals across the posterior portion of the eye. In particular, the controller alternately activates the first, second, third and fourth lasers such that a different laser is activated while the laser signals are scanned along different scan lines of the same frame. For example, the controller may activate the first laser while the scanner scans the laser signals emitted by the first laser across the first scan line. The controller may then activate the second laser while the scanner scans the laser signals emitted by the second laser along the second scan line. The controller then activates the third laser while the scanner scans the laser signals emitted by the third laser along the third scan line, before finally activating the fourth laser while the scanner scans the laser signals emitted by the fourth laser along the fourth scan line. The controller can then repeat this process by alternately activating the first, second, third and fourth lasers while the scanner scans the respective laser signals along the different scan lines until each of the scan lines of the same frame has been completed.

The optical scanning spectroscopic apparatus can also include means, such as a computer, for deinterlacing the data frame to form a plurality of images. In this regard, each image is generated in response to illumination of the posterior portion of the eye by laser signals emitted by different ones of the plurality of lasers. For example, in the embodiment in which the controller alternately activates the plurality of lasers such that only a single laser is activated at any one time, the plurality of resulting images are monochromatic. In the embodiment in which the optical scanning spectroscopic apparatus includes first, second, third and fourth lasers, for example, the four resulting monochromatic images will have been separately generated in response to illumination in the posterior portion of the eye by laser signals emitted by the first, second, third and fourth lasers, respectively.

The optical scanning spectroscopic apparatus can also include other components. For example, the optical scanning spectroscopic apparatus can include a target laser for illuminating the posterior portion of the eye in order to generate a corresponding image. Once the target laser illuminates a predetermined area of the posterior portion of the eye, the controller activates the plurality of lasers to begin the scanning process that forms the data frame. In order to appropriately filter the signals returning from the posterior portion of the eye, the optical scanning spectroscopic apparatus can also include an orthogonal polarizer. Since the plurality of lasers of this embodiment emit linearly polarized laser signals, the orthogonal polarizer will block the linearly polarized laser signals, such as the return signals reflected from the surface of the retinal vessels that maintain the same polarization, while passing the orthogonally polarized signals, such as the return signals that are transmitted through the blood within the retinal vessels prior to diffusing laterally and scattering back out of the eye, to the detector. In addition, the optical scanning spectroscopic apparatus can include at least one of a confocal filter and an anti-confocal filter positioned upstream of the detector for further selecting or filtering the signals to be delivered to the detector.

According to one aspect of the present invention, the optical scanning spectroscopic method and apparatus can also include a triggering mechanism for providing a trigger signal indicative of a predetermined point in a cardiac cycle of the subject. For example, the triggering mechanism can provide a trigger signal in response to an r-wave of an electrocardiogram (EKG) of the subject. The controller of this embodiment can therefore activate the one or more of the lasers in response to the trigger signal such that the posterior portion of the eye is illuminated during at least a predetermined portion of the cardiac cycle of the subject. The controller can activate the laser immediately upon receiving the trigger signal or the optical scanning spectroscopic apparatus can include a timer for delaying activation of the laser by at least a predetermined time following receipt of the trigger signal. In either instance, a data frame can be captured based upon the return signals relating to at least the predetermined portion of the cardiac cycle of the subject. As such, the optical scanning spectroscopic method and apparatus of this aspect of the invention can collect data that is specific to one or more phases of the cardiac cycle of the subject which may be particularly important for certain diagnostic or analytical applications.

The optical scanning spectroscopic method and apparatus of the present invention therefore illuminates the posterior portion of an eye with the laser signals emitted by a plurality of lasers having different respective wavelengths. However, by alternately illuminating the posterior portion of the eye with different ones of the plurality of lasers, the eye is not simultaneously subjected to illumination from each of the lasers, thereby protecting the eye from exposure to excessive illumination. As such, the intensity of the laser signals emitted by the lasers need not be reduced in order to protect the eye. Instead, the lasers can be operated at greater intensity levels than the lasers of those scanning laser opthalmoscopes that simultaneously illuminate the eye with the laser signals emitted by a plurality of lasers. As such, the signal-to-noise ratio of the signals returning from the posterior portion of the eye and detected according to the present invention is greater than the signal-to-noise ratio of the return signals detected by those scanning laser opthalmoscopes that simultaneously illuminate the eye with laser signals emitted a plurality of lasers as a result of the increased intensity of the laser signals emitted by the lasers. Thus, fewer signals returning from the posterior portion of the eye will be lost in the noise and the validity of the detected signals will be more reliable. By alternately illuminating the posterior portion of the eye with laser signals emitted by different ones of the lasers, the resulting data frame includes interlaced portions formed from signals returning from the posterior portion of the eye in response to illumination by laser signals emitted by different ones of plurality of lasers. The optical scanning spectroscopic method and apparatus of the present invention are therefore capable of alternately scanning the posterior portion of the eye with the laser signals emitted by different lasers in a rapid fashion such that the measurement conditions, such as the position of the subject and the constriction of the subject's pupil, do not change appreciably between the times at which the subject's eye is illuminated by different lasers. As such, the resulting images generated in response to illumination of the posterior portion of the eye by laser signals emitted by different ones of the lasers should be more consistent and more easily correlated than sequential data frames generated by the illumination of the subject's eye with the different lasers.

DETAILED DESCRIPTION OF THE INVENTION

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

Figure 1:
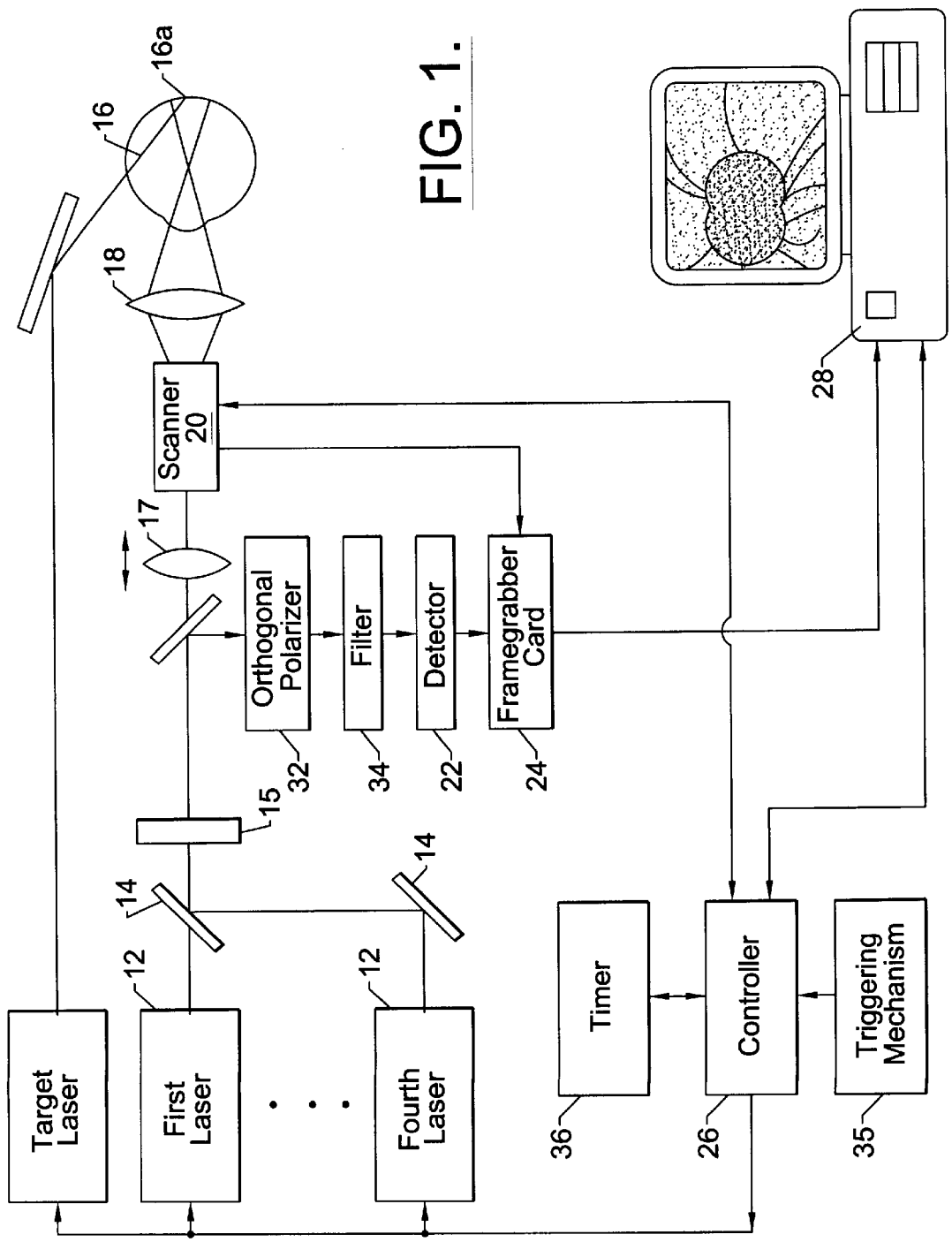
FIG. 1 is a block diagram illustrating an optical scanning spectroscopic apparatus according to one advantageous embodiment of the present invention.

Referring now to FIG. 1, an optical scanning spectroscopic apparatus 10 according to one embodiment of the present invention is depicted. The optical scanning spectroscopic apparatus includes a plurality of lasers 12 for emitting laser signals having different respective wavelengths. While the optical scanning spectroscopic apparatus can include any number of lasers, such as three lasers or five lasers, the optical scanning spectroscopic apparatus of one advantageous embodiment includes first, second, third and fourth lasers for emitting laser signals having first, second, third and fourth wavelengths, respectively.

According to the present invention, the plurality of lasers 12 can be selected so as to have any combination of wavelengths. Most commonly, however, the lasers are selected so as to emit laser signals having wavelengths that are appropriate for the particular application. For example, in order to monitor the blood oxygen saturation or blood oxygen content of the blood in retinal vessels, the optical scanning spectroscopic apparatus 10 preferably includes first, second, third and fourth lasers that emit laser signals having wavelengths of 488 nm, 635 nm, 670 nm and 830 nm, respectively. In order to measure other anatomic features or physiological parameters, however, the optical scanning spectroscopic apparatus can include a plurality of lasers that emit laser signals having different wavelengths, if so desired. The lasers 12 can also be physically embodied in different manners without departing from the spirit and scope of the present invention. Typically, however, the lasers are diode lasers.

As shown in FIG. 1, the optical scanning spectroscopic apparatus 10 also includes one or more beam combiners 14, such as one or more dichroic beam combiners, for combining the laser signals emitted by the plurality of lasers to form a composite beam having each of the different respective wavelengths. Although the signals emitted by the lasers 12 are polarized, the optical scanning spectroscopic apparatus can also include a polarizer 15 for guaranteeing the polarization of the laser signals. The combined beam is then directed so as to illuminate the posterior portion 16a of a subject's eye 16. Depending upon the application, different areas of the posterior portion of the subject's eye can be illuminated. For example, an optical scanning spectroscopic apparatus designed to measure the blood oxygen content of the retinal vessels would illuminate the retina including the retinal vessels disposed along the rear surface of the eye. Alternatively, in order to monitor choroidal oxygenation, the composite beam can be directed to illuminate the choroid including the choroidal vessels. While the composite beam can be directed in a number of different fashions, the optical scanning spectroscopic apparatus of the illustrated embodiment includes one or more lenses. For example, the optical scanning spectroscopic apparatus can include a focusing lens 17 that is adapted to translate (as illustrated by the double-ended arrow) in order to focus the composite beam while compensating for refractive errors, such as nearsightedness or farsightedness. The optical scanning spectroscopic apparatus can also include an imaging lens 18 for imaging the composite beam onto the pupil of the subject's eye.

The optical scanning spectroscopic apparatus 10 is designed to repeatedly scan the laser signals emitted by the plurality of lasers 12 across the posterior portion 16a of the eye 16. As such, the optical scanning spectroscopic apparatus also includes a scanner 20. While the optical scanning spectroscopic apparatus can include a variety of scanners, the scanner of one advantageous embodiment is a two-axis scanner having a VSH-8 kHz video scan head that is provided by General Scanning, Inc. In more detail, the two-axis scanner includes one galvanometer scanner and one resonant scanner. Preferably, the scanner raster scans the laser signals in a predetermined pattern across the posterior portion of the eye to thereby define a frame having a plurality of scan lines. For example, one conventional scanner scans the laser signals in a predetermined pattern consisting of 512 scan lines arranged in a generally square pattern within a relatively short time, such as 77 msec.

According to the present invention, the optical scanning spectroscopic apparatus 10 also preferably includes a detector 22, such as a photodetector, for detecting signals returning from the posterior portion 16a of the eye 16 in response to illumination by the laser signals. In this regard, the detector typically measures the intensity of the light reflected from the posterior portion of the eye, including the light scattered and reflected by the retinal and choroidal vessels. As a result of the scanning of the laser signals in a predetermined pattern of scan lines across the posterior portion of the eye, the return signals are also arranged in the predetermined pattern. In one advantageous embodiment, the detector, such as an avalanche photodiode or a photomultiplier tube, detects the return signals on a pixel by pixel basis. The detector then transfers the pixel to a means, such as a frame grabber card 24, for constructing a data frame from the pixels provided by the detector. While a variety of frame grabber cards can be utilized, one conventional frame grabber card is a Matrox Pulsar card.

The data frame constructed by the frame grabber card can be shaped and sized in different manners. However, the shape and size of the data frame typically corresponds to the shape and size of the predetermined pattern established by the scanner 20. In this regard, the data frame constructed by the frame grabber card typically has the same number of lines as the number of scan lines. In one embodiment, for example, the data frame includes 512 lines, each of which is formed of 512 pixels, to thereby form a data frame that is sized to be 512 pixels×512 pixels. In order to insure that the framegrabber card constructs a data frame that corresponds to the predetermined pattern established by the scanner, the scanner typically provides control signals to the framegrabber card that consist of a vertical sync signal that indicates that a new frame is about to begin, a horizontal sync signal that indicates that a new line is about to begin and a pixel clock that indicates that a new pixel is being generated.

As depicted in FIG. 1, the optical scanning spectroscopic apparatus 10 preferably includes a controller 26 for alternately activating different ones of the plurality of lasers 12 while the scanner 20 scans the laser signals across the posterior portion 16a of the eye 16. In one example in which the optical scanning spectroscopic apparatus includes first, second, third and fourth lasers, the controller alternately activates the first, second, third and fourth lasers such that a different one of the lasers is activated while the laser signals are scanned along different scan lines of the same frame. For example, the controller can initially activate the first laser while the scanner scans the laser signals emitted by the first laser along a first scan line across the posterior portion of the eye. The controller then deactivates the first laser and activates the second laser while the scanner scans the laser signals emitted by the second laser along the second scan line across the posterior portion of the eye. Thereafter, the controller deactivates the second laser and activates the third laser while the scanner scans the laser signals emitted by the third laser along a third scan line across the posterior portion of the eye. Finally, the controller deactivates the third laser and activates the fourth laser while the scanner scans the laser signals emitted by the fourth laser along a fourth scan line across the posterior portion of the eye. Thereafter, the controller alternately activates the first, second, third and fourth lasers as the scanner scans the laser signals across the fifth, sixth, seventh and eighth scan lines, respectively, across the posterior portion of the eye. See FIG. 2. The controller then repeats this alternate activation of the first, second, third and fourth lasers until each of the scan lines of the frame has been completed. Although the optical scanning spectroscopic apparatus of the above example includes four lasers, the optical scanning spectroscope apparatus can include more or fewer lasers, if so desired.

While the controller 26 of the foregoing example alternately activates a single laser 12 while the scanner 20 scans the laser signals emitted by the laser along a scan line across the posterior portion 16a of the eye 16, the controller can concurrently activate two or more lasers while the scanner scans the laser signals emitted by the activated lasers along a scan line across the posterior portion of the eye. According to the present invention, however, the controller activates different ones or different combinations of the lasers while the scanner is scanning the laser signals across the posterior portion of the eye during the generation of a single data frame. In addition, while the controller of the above example activates different lasers for each scan line, the controller can activate different lasers at other intervals during the generation of a single data frame, such as by activating a different laser to generate each pixel of a data frame. However, the controller of the optical scanning spectroscopic apparatus 10 of the present invention need only activate a different laser or a different combination of lasers at some point while the scanner is scanning the laser signals in a predetermined pattern across the posterior portion of the eye such that different portions of the same data frame are based upon signals returning from the posterior portion of the eye in response to illumination by laser signals emitted by different lasers.

Figure 2:
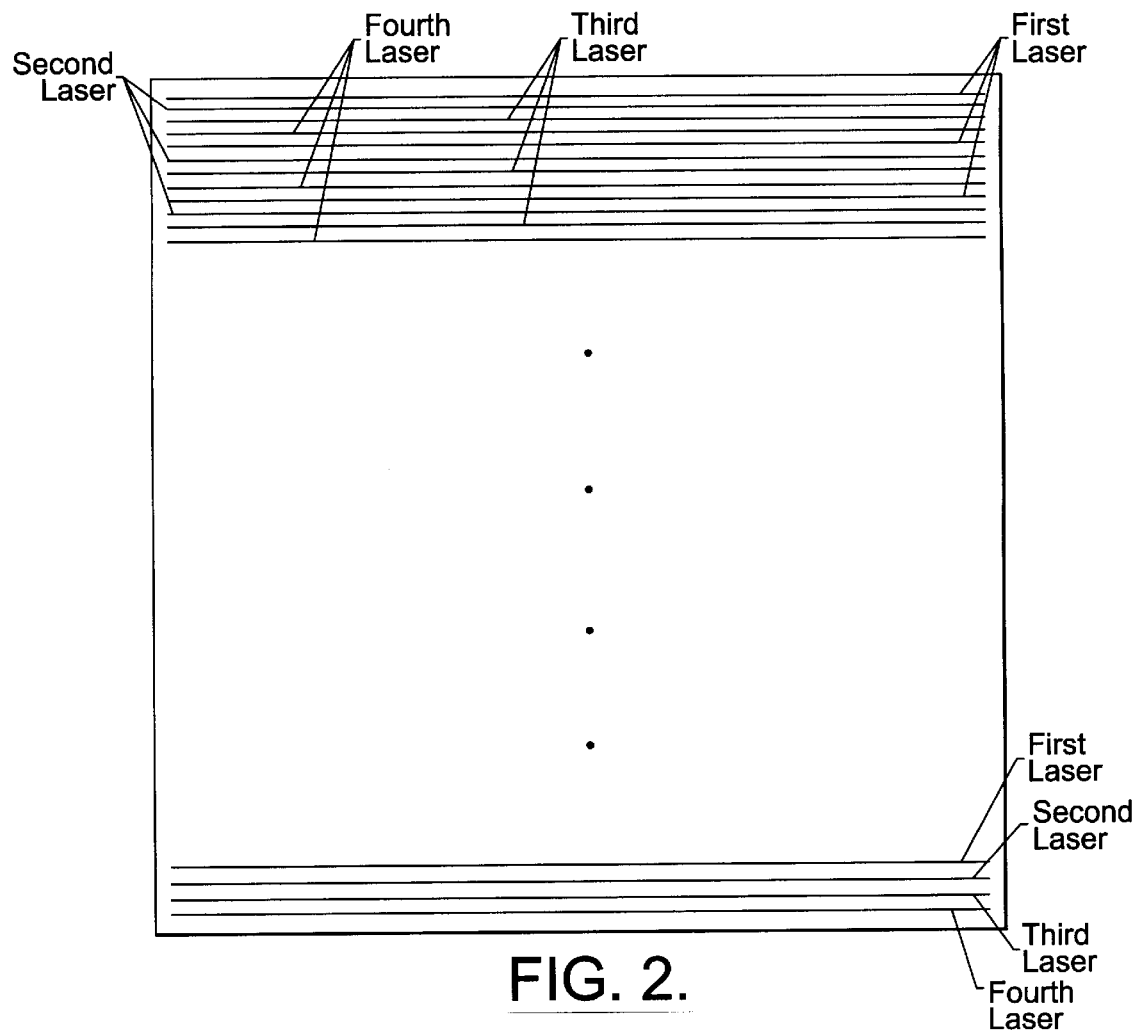
FIG. 2 is a schematic representation of a portion of a data frame generated according to the optical scanning spectroscopic method and apparatus of one embodiment of the present invention that indicates the source of the laser signals that generated the respective scan line.

Since different ones of the plurality of lasers 12 are alternately activated by the controller 26 while the scanner 20 scans the laser signals across the posterior portion 16a of the eye 16, the data frame constructed by the detector 22 based upon the signals returning from the posterior portion of the eye includes a plurality of interlaced portions, adjacent ones of which are formed from return signals in response to illumination by laser signals emitted by different ones or different combinations of the lasers. As shown in FIG. 2, for example, the data frame constructed as a result of the alternate activation of the first, second, third and fourth lasers for each scan line is depicted. As shown, the first, fifth and ninth lines of the data frame are attributable to return signals generated in response to illumination by the first laser. Likewise, the second, sixth and tenth lines of the data frame are attributable to return signals generated in response to the illumination by the second laser. Further, the third, seventh, and eleventh lines of the data frame are attributable to return signals generated by the illumination by the third laser, while the fourth, eighth and twelfth lines of the data frame are attributable to return signals generated by the illumination by the fourth laser. As such, each line of the data frame of this embodiment is an interlaced portion. However, the interlaced portions can be larger, such as two or more lines, or smaller, such as one or more pixels, depending upon the manner in which the controller alternately activates different ones of the plurality of lasers as described above.

Figure 3:
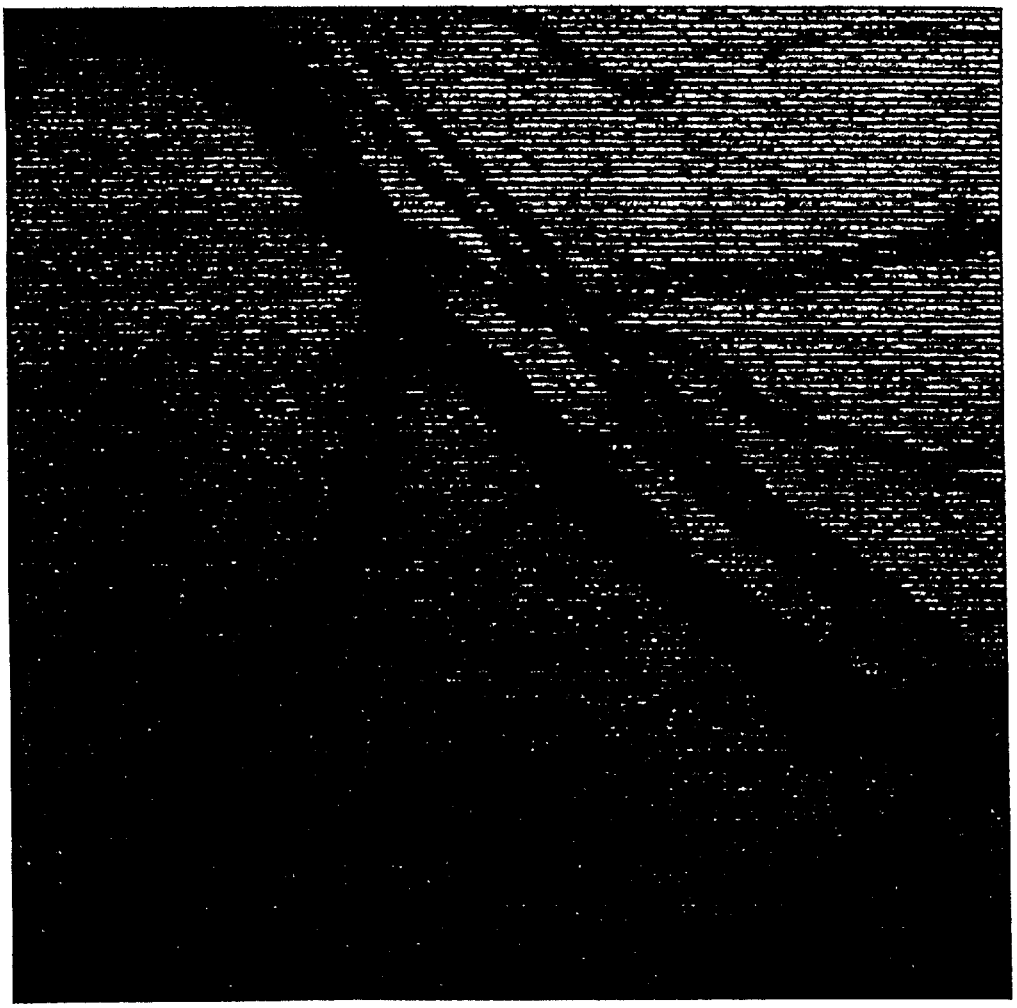
FIG. 3 is a data frame having a number of interlaced portions that was obtained by the optical scanning spectroscopic method and apparatus of one embodiment of the present invention.
Figure 4A:
FIGS. 4A–4D are the monochromatic images formed by deinterlacing the interlaced portions of the data frame of FIG. 3 wherein each monochromatic image is generated in response to the illumination of the posterior portion of the eye by laser signals emitted by a different laser of the optical scanning spectroscopic apparatus of the present invention.
Figure 4B:
Figure 4C:
Figure 4D:
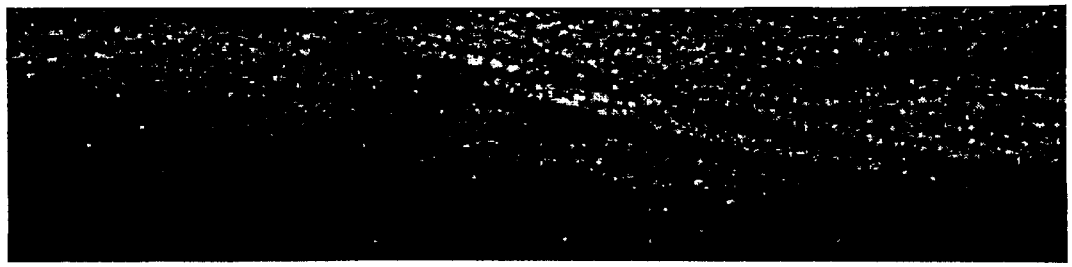

As depicted in FIG. 1, the optical scanning spectroscopic apparatus 10 also generally includes means, such as a computer 28, a processor or the like, for de-interlacing the data frame to form a plurality of images. In this regard, each resulting image will have been generated in response to the illumination of the posterior portion 16a of the eye 16 by laser signals emitted by different ones of the plurality of lasers 12. In the above example in which the optical scanning spectroscopic apparatus includes first, second, third and fourth lasers that alternately illuminate the posterior portion of the eye, the resulting data frame can be de-interlaced to form first, second, third and fourth images generated in response to the illumination of posterior portion of the eye by laser signals emitted by the first, second, third and fourth lasers, respectively. By way of example, a data frame having a number of interlaced portions is depicted in FIG. 3. In addition, the resulting images that are constructed upon de-interlacing the data frame of FIG. 3 are depicted in FIGS. 4A–4D which are attributable to the illumination of posterior portions of the eye by the first, second, third and fourth lasers, respectively. As such, in instances in which the controller alternately activates the plurality of lasers such that only a single laser is activated at any one time, such as described above in conjunction with the embodiment that includes first, second, third and fourth lasers, the means for de-interlacing the data frame forms a plurality of monochromatic images, each being attributable to laser signals having a single wavelength.

By interlacing portions attributable to illumination by different ones of the lasers 12, the speed and responsiveness of one optical scanning spectroscopic method and apparatus 10 is equivalent to that of those scanning laser opthalmoscopes that simultaneously illuminate the eye with signals generated by each of a plurality of lasers. As a result of dividing the data frame into a plurality of interlaced portions, however, the vertical resolution of the image created upon de-interlacing the portions will be less than the vertical resolution of the images captured by other scanning laser opthalmoscopes. However, the resolution of the images created upon de-interlacing the portions of the data frame should still be sufficient for most, if not all, applications.

Although not necessary for the practice of the present invention, the optical scanning spectroscopic apparatus 10 can also include a target laser 30, such as an infrared laser, for illuminating the posterior portions 16a of the eye 16 with relatively low levels of infrared signals. While the target laser is depicted as a separate laser from the primary lasers 12 in FIG. 1, one of the primary lasers, i.e., the first, second, third or fourth laser, can also serve as the target laser, if so desired. By detecting the signals returning from the posterior portions of the eye in response to illumination by the target laser, the detector 22 in conjunction with the frame grabber card 24, can obtain a video image of the posterior portion of the eye. Among other things, this video image can be displayed upon a display for visual analysis by the system operator and/or provided to the computer for automated analysis. Upon detecting a desired feature or area, such as the retinal vessels and/or the choroidal vessels that appear as dark lines emanating from the optic nerve, the relative positions of the subject and the optical scanning spectroscopic apparatus 10 are fixed. The controller 26 can then deactivate the target laser (if a separate target laser is employed) and activate one or more of the primary lasers 12 for beginning the scanning process to illuminate the desired area of the posterior portion of the eye and to collect data relating thereto. As such, the target laser provides a mechanism by which the desired area of the posterior portion of the eye can be specifically located prior to collecting data.

In addition, the optical scanning spectroscopic apparatus 10 can include various types of filters in order to appropriately condition the return signals presented to the detector 22. In this regard, the optical scanning spectroscopic apparatus can include an orthogonal polarizer 32 positioned upstream of the detector. Since the plurality of lasers 12 emit linearly polarized laser signals, the orthogonal polarizer will filter out or block the return signals that have the same linear polarization since most of these return signals have reflected from the outer surface of the retinal vessels and do not include information relating to the oxygenation of the blood or the like. As such, the polarized signals are preferably never presented to the detector and do not skew or otherwise disadvantageously alter the data frame constructed by the detector and the frame grabber card 24. However, the orthogonal polarizer will permit the orthogonally polarized return signals that are primarily attributable to the laser signals that have been scattered and that include information relating to the blood oxygen saturation or the like.

The optical scanning spectroscopic apparatus 10 can include other types of filters 34, such as a confocal filter or an anti-confocal filter, positioned upstream of the detector 22. As known to those skilled in the art, a confocal filter and an anti-confocal filter are designed to permit return signals that have been reflected and/or scattered from different depths within the posterior portion 16a of the eye 16 to be presented to the detector. In this regard, a confocal filter generally defines a pin hole such that return signals that are reflected or scattered from the surface of the posterior portion of the eye pass through the pin hole and are presented to the detector, while all other return signals that have been scattered from deeper regions are filtered out. Conversely, an anti-confocal filter, such as a glass plate having a silver dot thereupon, or a glass plate having a ring-shaped region that is translucent, if not transparent, but that is otherwise coated with silver or the like, filters out the return signals attributable to the laser signals that are reflected or scattered by the surface of the posterior portion of the eye and, instead, permits the return signals that have been reflected or scattered from regions below or behind the surface of the posterior portion of the eye to be detected.

The optical scanning spectroscopic method and apparatus 10 of the present invention can be activated during any portion of the cardiac cycle of a subject. In some applications, however, the optical scanning spectroscopic method and apparatus is preferably controlled so as to monitor the posterior portion 16a of the eye 16 and obtain data relating thereto during one or more predetermined portions of the cardiac cycle of the subject. As such, the optical scanning spectroscopic apparatus of this embodiment can also include a triggering mechanism 35 for providing a trigger signal indicative of a predetermined point in a cardiac cycle of the subject. While various types of triggering mechanisms can be employed, the triggering mechanism of one advantageous embodiment provides a trigger signal in response to an r-wave of an electrocardiogram (EKG) of the subject. As known to those skilled in the art, the r-wave is an electrical signal generated by the heart at the beginning of ventricular contraction. As such, the triggering mechanism can be an EKG machine that generates an EKG and provides a number of outputs, including the r-wave.

Upon receiving the trigger signal, the controller 26 can immediately activate one or more of the lasers 12 in order to illuminate the subject's eye 16 and to begin collecting data. Alternatively, the controller can be adapted to activate one or more of the lasers at some predetermined time following the receipt of the trigger signal. In this regard, the optical scanning spectroscopic apparatus 10 can also include a timer 36 that is responsive to the triggering mechanism 34. While the timer can be a separate component, the timer can also form a portion of the controller, if so desired. Upon receipt of the trigger signal, the timer is activated. Once the timer has determined that a predetermined time has elapsed since receipt of the trigger signal, the timer will issue a signal notifying the controller. The controller can then activate the lasers in order to illuminate the subject's eye to begin collecting data.

In most instances, the plurality of lasers 12 are scanned across the posterior portion 16a of the eye 16 as described above. In this regard,-the scanner 20, such as the two-axis scanner provided by General Scanning, Inc., periodically issues vertical sync signals indicative of the commencement of another frame and horizontal sync signals indicative of the commencement of another line. As such, upon receipt of a signal from the timer 36 representing that a predetermined time has elapsed since the receipt of the trigger signal, the controller 26 awaits receipt of the next vertical sync signal from the scanner. Upon receipt of the next vertical sync signal, the controller then monitors the horizontal sync signal issued by the scanner. Upon receipt of the first horizontal sync signal following the vertical sync signal, the controller activates at least one of the lasers in order to illuminate the posterior portion of the eye. The controller also issues a signal to the timer that stops the timer such that the value of the timer is representative of the actual delay time from receipt of the trigger signal to activation of the lasers. The timer can subsequently report the actual delay time to the controller for further analysis. The controller can then alternately activate each of the lasers as each subsequent line is scanned, as described above.

According to this embodiment of the present invention, the optical scanning spectroscopic apparatus 10 can obtain images of the posterior portion 16a of the eye 16 during predetermined portions of the cardiac cycle of the subject. As such, more detailed or specific information relating to the performance of the subject during predetermined phases of the cardiac cycle can be obtained for diagnostic and/or analytical purposes.

Figure 5:
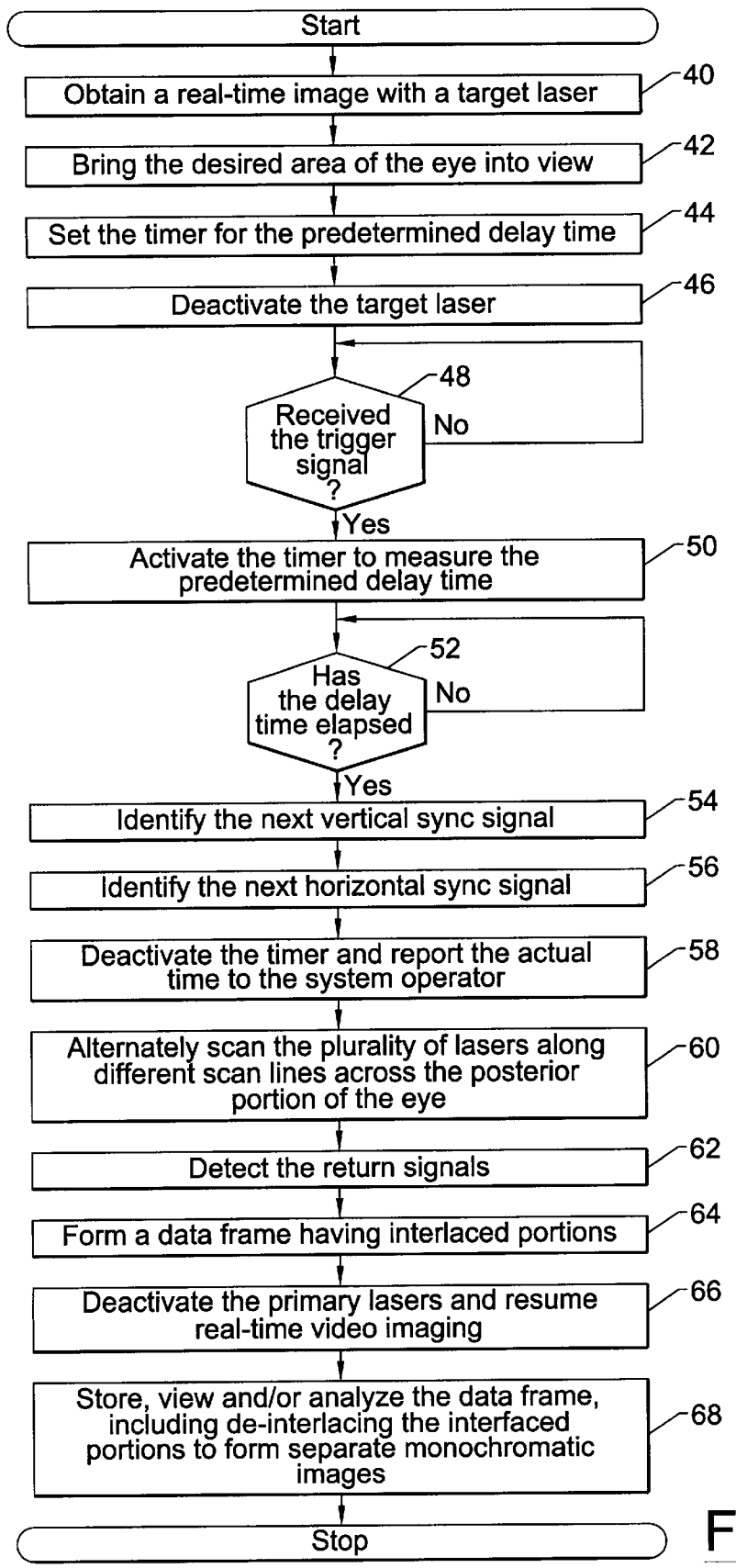
FIG. 5 is a flow chart illustrating the operations performed by the optical scanning spectroscopic method and apparatus according to one advantageous embodiment of the present invention.

While the method of operation has been described heretofore in conjunction with the various components of the optical scanning spectroscopic apparatus 10, the method of one advantageous embodiment is described hereinbelow for purposes of clarity and with reference to FIG. 5. As will be apparent, the subsequently described method includes an embodiment of the optical scanning spectroscopic apparatus that includes a target laser 30 and a triggering mechanism 35. However, the optical scanning spectroscopic apparatus need not include a target laser or a triggering mechanism.

By way of illustration, the method of one advantageous embodiment initially illuminates the posterior portion 16a of a subject's eye 16 with a target laser 30, such as an infrared laser, to obtain a real-time image of the posterior portion of the eye. See block 40. The operator then repositions the optical scanning spectroscopic apparatus 10 and/or the subject until the desired area of the posterior portion of the eye is in view. See block 42. In this embodiment in which a predetermined portion of the cardiac cycle of the subject is to be analyzed, the operator also sets the timer 36 to a predetermined delay time indicative of the delay to be inserted after receipt of the trigger signal prior to illuminating the posterior portion of the eye with the primary lasers 12 and obtaining data. See block 44. Once the desired area of the posterior portion of the eye is identified, the operator deactivates the targeting laser (if separate target and primary lasers are employed) and presses a key or otherwise indicates that the posterior portion of the eye should be scanned following receipt of the next trigger signal. See block 46. Upon receipt of a trigger signal, such as in response to the next r-wave of the subject's EKG, the controller 26 activates the timer to provide the predetermined delay time. See blocks 48 and 50. Once the timer indicates that the predetermined delay time has elapsed, the controller monitors the scanner 20 to identify the next vertical sync signal indicative of the commencement of the next frame. See blocks 52 and 54. Upon receipt of a vertical sync signal, the controller continues to monitor the scanner to identify the next horizontal sync signal indicative of the commencement of the first line of the new frame. See block 56. Upon receiving the next horizontal sync signal, the controller stops the timer such that the value of the timer is the actual delay time. See block 58. The timer can then report the actual delay time to the controller for further analysis.

The controller 26 then activates a first one of the lasers 12 that is scanned across the first line of the new frame. Upon completion of the first line, the first laser is deactivated and a second laser is activated so as to be scanned across the second line of the new frame. Thereafter, the second laser is deactivated and a third laser is scanned across the third line of the new frame. Finally, the third laser is deactivated and a fourth laser is scanned across the fourth line of the new frame. The controller then repeats this process of alternately activating the first, second, third and fourth lasers until the scanner 20 has scanned all of the lines of the frame. See block 60. During the scanning process, the detector 22 also detects signals returning from the posterior portion 16a of the eye 16 and communicates the detected return signals to the frame grabber card 24, to form a data frame having a number of interlaced portions or lines that are representative of return signals that were generated in response to illumination by the first, second, third and fourth lasers. See blocks 62 and 64. Once the entire frame has been completed, the lasers are all deactivated and the target laser 30 can again be activated to obtain real time video. See block 66. Thereafter, the data frame can be stored, viewed and/or otherwise analyzed. For example, the interlaced portions or lines can be de-interlaced such that separate images are formed for those return signals generated in response to illumination by the first, second, third and fourth lasers. See block 68.

In addition, by recording the actual delay time, the predetermined portion of the cardiac cycle of the subject can be identified in order to assist in the diagnostic and/or analysis process. Since the frames are generally acquired at regular intervals as defined by the operation of the scanner 20, such as about 15 frames per second, the actual delay time will typically be somewhat larger than the predetermined delay time set by the operator since the controller 26 must await commencement of the next frame following expiration of the preset delay time prior to activating the lasers 12 and beginning to gather additional data. By identifying the actual delay time, however, the optical scanning spectroscopic method and apparatus 10 of this embodiment of the present invention can still precisely identify the portion of the cardiac cycle of the subject that is occurring while the data is being collected.

The optical scanning spectroscopic method and apparatus 10 of the present invention therefore illuminates the posterior portion 16a of an eye 16 with the laser signals emitted by a plurality of lasers 12 having different respective wavelengths. However, by alternately illuminating the posterior portion of the eye with different ones of the plurality of lasers, the eye is not simultaneously subjected to illumination from each of the lasers, thereby protecting the eye from exposure to excessive illumination. As such, the intensity of the laser signals emitted by the lasers need not be reduced in order to protect the eye. Instead, the lasers can be operated at greater intensity levels than the lasers of those scanning laser opthalmoscopes that simultaneously illuminate the eye with the laser signals emitted by a plurality of lasers. As such, the signal-to-noise ratio of the signals returning from the posterior portion of the eye and detected according to the present invention is greater than the signal-to-noise ratio of the return signals detected by those scanning laser opthalmoscopes that simultaneously illuminate the eye with laser signals emitted by different lasers, as a result of the increased intensity of the laser signals emitted by the lasers. Thus, fewer signals returning from the posterior portion of the eye will be lost in the noise and the validity of the detected signals will be more reliable. By alternately illuminating the posterior portion of the eye with laser signals emitted by different ones of the lasers, the resulting data frame includes interlaced portions formed from signals returning from the posterior portion of the eye in response to illumination by laser signals emitted by different ones of plurality of lasers. The optical scanning spectroscopic method and apparatus of the present invention is therefore capable of alternately scanning the posterior portion of the eye with the laser signals emitted by different lasers in a rapid fashion such that the measurement conditions, such as the position of the subject and the constriction of the subject's pupil, do not change appreciably between the times at which the subject's eye is illuminated by different lasers. As such, the resulting images generated in response to illumination of the posterior portion of the eye by laser signals emitted by different ones of the lasers should be more consistent and more easily correlated than sequential data frames generated by illumination of the subject's eye with the different lasers.

Many modifications and other embodiments of the invention will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. An optical scanning spectroscopic apparatus comprising:
   a plurality of lasers for emitting laser signals having different respective wavelengths;
   a scanner for repeatedly scanning the laser signals emitted by said plurality of lasers across a posterior portion of an eye;
   a detector for detecting signals returning from the posterior portion of the eye in response to illumination by the laser signals to thereby form a data frame comprising a plurality of interlaced portions; and
   a controller for alternately activating different ones of said plurality of lasers while said scanner scans the laser signals across the posterior portion of the eye such that adjacent interlaced portions of the data frame are formed from signals returning from the posterior portion of the eye in response to illumination by laser signals emitted by different ones of said plurality of lasers.

2. An optical scanning spectroscopic apparatus according to claim 1 further comprising means for deinterlacing the data frame to form a plurality of images, wherein each image is generated in response to illumination of the posterior portion of the eye by laser signals emitted by different ones of said plurality of lasers.

3. An optical scanning spectroscopic apparatus according to claim 2 wherein said controller alternately activates said plurality of lasers such that a single laser is activated at any one time, and wherein said means for deinterlacing the data frame forms a plurality of monochromatic images.

4. An optical scanning spectroscopic apparatus according to claim 1 further comprising a triggering mechanism for providing a trigger signal indicative of a predetermined point in a cardiac cycle of a subject, wherein said controller activates at least one of said plurality of lasers in response to the trigger signal such that the posterior portion of the subject's eye is illuminated during at least a predetermined portion of the cardiac cycle of the subject.

5. An optical scanning spectroscopic apparatus according to claim 4 wherein said triggering mechanism provides a trigger signal in response to an r-wave of an electrocardiogram (EKG) of the subject.

6. An optical scanning spectroscopic apparatus according to claim 4 further comprising a timer, responsive to said triggering mechanism, for delaying activation of at least one of said plurality of lasers by at least a predetermined time following receipt of the trigger signal.

7. An optical scanning spectroscopic apparatus according to claim 1 further comprising a target laser for illuminating the posterior portion of the eye in order to generate a corresponding image, wherein said controller deactivates said target laser and activates said plurality of lasers once said target laser illuminates a predetermined area of the posterior portion of the eye.

8. An optical scanning spectroscopic apparatus according to claim 1 wherein said plurality of lasers emit linearly polarized laser signals, and wherein the optical scanning spectroscopic apparatus further comprises an orthogonal polarizer positioned upstream of said detector for only passing to said detector those signals returning from the posterior portion of the eye that are orthogonally polarized.

9. An optical scanning spectroscopic apparatus according to claim 1 further comprising at least one of a confocal filter and an anti-confocal filter positioned upstream of said detector.

10. An optical scanning spectroscopic apparatus comprising:
   first, second, third and fourth lasers for emitting laser signals having first, second, third and fourth wavelengths, respectively;
   a scanner for repeatedly scanning the laser signals emitted by said first, second, third and fourth lasers in a predetermined pattern across a posterior portion of an eye to thereby define a frame comprising a plurality of scan lines; and
   a controller for alternately activating said first, second, third and fourth lasers while said scanner scans the laser signals across the posterior portion of the eye, said controller alternately activating said first, second, third and fourth lasers such that a different laser is activated while the laser signals are scanned along different scan lines of the same frame.

11. An optical scanning spectroscopic apparatus according to claim 10 further comprising a detector for detecting signals returning from the posterior portion of the eye in response to illumination by the laser signals to thereby form a data frame comprising a plurality of interlaced portions.

12. An optical scanning spectroscopic apparatus according to claim 11 further comprising means for deinterlacing the data frame to form a plurality of monochromatic images, wherein each monochromatic image is generated in response to illumination of the posterior portion of the eye by laser signals emitted by a different laser.

13. An optical scanning spectroscopic apparatus according to claim 10 further comprising a triggering mechanism for providing a trigger signal indicative of a predetermined point in a cardiac cycle of a subject, wherein said controller activates at least one of said first, second, third and fourth lasers in response to the trigger signal such that the posterior portion of the subject's eye is illuminated during at least a predetermined portion of the cardiac cycle of the subject.

14. An optical scanning spectroscopic apparatus according to claim 13 wherein said triggering mechanism provides a trigger signal in response to an r-wave of an electrocardiogram (EKG) of the subject.

15. An optical scanning spectroscopic apparatus according to claim 13 further comprising a timer, responsive to said triggering mechanism, for delaying activation of at least one of said first, second, third and fourth lasers by at least a predetermined time following receipt of the trigger signal.

16. An optical scanning spectroscopic apparatus according to claim 10 further comprising a target laser for illuminating the posterior portion of the eye in order to generate a corresponding image, wherein said controller deactivates said target laser and activates at least one of said first, second, third and fourth lasers once said target laser illuminates a predetermined area of the posterior portion of the eye.

17. A method for optically scanning a posterior portion of an eye, the method comprising:
   alternately scanning laser signals having different wavelengths across the posterior portion of the eye;
   detecting signals returning from the posterior portion of the eye in response to illumination by the laser signals; and
   forming a data frame comprising a plurality of interlaced portions,
   wherein laser signals having different wavelengths are alternately scanned across the posterior portion of the eye such that adjacent interlaced portions of the data frame are formed from signals returning from the posterior portion of the eye in response to illumination by laser signals having different wavelengths.

18. A method according to claim 17 further comprising deinterlacing the data frame to form a plurality of images, wherein each image is generated in response to illumination of the posterior portion of the eye by laser signals having different wavelengths.

19. A method according to claim 17 further comprising providing a trigger signal indicative of a predetermined point in a cardiac cycle of a subject, wherein scanning the laser signals is initiated in response to the trigger signal such that the posterior portion of the subject's eye is illuminated during at least a predetermined portion of the cardiac cycle of the subject.

20. A method according to claim 19 wherein receiving the trigger signal comprises receiving the trigger signal in response to an r-wave of an electrocardiogram (EKG) of the subject.

21. A method according to claim 19 further comprising delaying illumination of the posterior portion of the eye by at least a predetermined time following receipt of the trigger signal.

22. A method according to claim 17 further comprising:

illuminating the posterior portion of the eye with laser signals emitted by a target laser in order to generate a corresponding image;

identifying a predetermined area of the posterior portion of the eye within the corresponding image; and deactivating the target laser and commencing the alternate scanning of laser signals having different wavelengths across the posterior portion of the eye following identification of the predetermined area of the posterior portion of the eye.

23. A method according to claim 22 wherein identifying a predetermined area of the posterior portion of the eye comprises automatically identifying the predetermined area of the posterior portion of the eye within the corresponding image.

* * * * *